US005466254A

United States Patent [19]
Helland

[11] Patent Number: 5,466,254
[45] Date of Patent: Nov. 14, 1995

[54] CORONARY SINUS LEAD WITH ATRIAL SENSING CAPABILITY

[75] Inventor: John R. Helland, Issaquah, Wash.

[73] Assignee: Pacesetter, Inc., Sylmar, Calif.

[21] Appl. No.: 125,447

[22] Filed: Sep. 22, 1993

[51] Int. Cl.⁶ ..................................... A61N 1/39
[52] U.S. Cl. ...................................... 607/123
[58] Field of Search ................... 607/121, 122, 607/123

[56] References Cited

U.S. PATENT DOCUMENTS

| | | | |
|---|---|---|---|
| 3,333,045 | 7/1967 | Fisher et al. | |
| 4,281,668 | 8/1981 | Richter et al. | 607/121 |
| 4,750,494 | 6/1988 | King | |
| 4,922,927 | 5/1990 | Fine et al. | 607/122 |
| 4,928,688 | 5/1990 | Mower | 607/9 |
| 5,099,838 | 3/1992 | Bardy | 607/122 |
| 5,165,403 | 11/1992 | Mehra | 607/122 |
| 5,269,319 | 12/1993 | Schulte et al. | 607/123 |

Primary Examiner—William E. Kamm
Assistant Examiner—Scott M. Getzow
Attorney, Agent, or Firm—Malcolm J. Romano

[57] ABSTRACT

A coronary sinus lead, for use in combination with an implanted pulse generator which may be a pacemaker or defibrillator or combination thereof. The coronary sinus lead can deliver an electrical charge to pace, cardiovert or defibrillate the heart, and can sense cardiac activity in the coronary sinus of the heart. The coronary sinus lead may include additional sensor electrodes capable of sensing electrical or physical activity in the atrial cavity. The coronary sinus lead allows cardioversion and/or defibrillation stimuli to be provided by a large surface area electrode which is passively implanted in the coronary sinus, to allow the pulse generator to provide appropriately synchronized atrial-ventricular pacing, cardioversion or defibrillation.

22 Claims, 3 Drawing Sheets

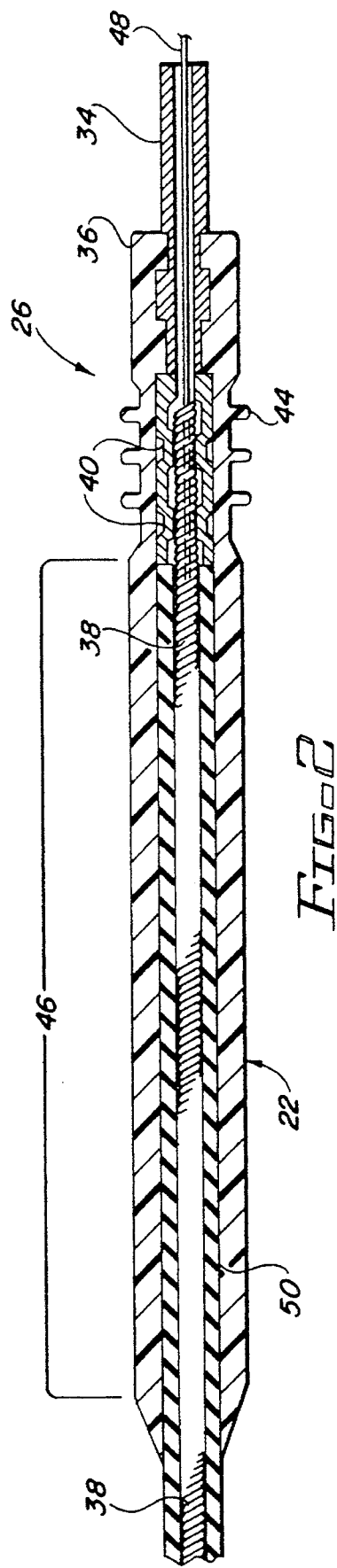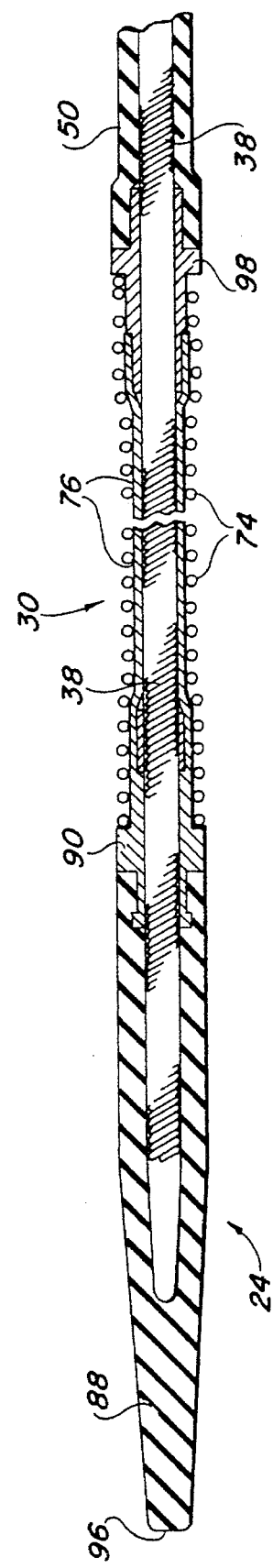

CORONARY SINUS LEAD WITH ATRIAL SENSING CAPABILITY

FIELD OF THE INVENTION

The present invention relates generally to medical electronic devices and, more particularly, to implantable devices for pacing, cardioverting or defibrillating a heart. Specifically, the present invention is directed to a lead designed to be placed into the coronary sinus which can pace, cardiovert or defibrillate the heart, and sense cardiac activity in the atrium or coronary sinus of the heart, in conjunction with an implanted pacemaker and/or defibrillator.

BACKGROUND OF THE INVENTION

A number of types of implantable devices are in use to monitor and control the electrical activity of the heart. For example, it is known to have an implanted pacemaker interconnected via a transvenous pacing lead to an electrode in intimate contact with the myocardial tissue of the heart. The electrode can both sense the electrical activity of the heart and deliver an electrical stimulus provided by the pacemaker when required. Other systems include pacemakers and transvenous pacing leads which have a variety of sensor electrodes proximally spaced behind the tip electrode of the pacing lead. The sensors provide information to the pacemaker. There are also systems which monitor and provide automatic defibrillation utilizing an implanted power source and an electrode system, either attached to the surface of or implanted within the heart. Still other systems combine the pacemaker function with an automatic defibrillation capability, and may include multiple leads extending to internal as well as external portions of the heart.

More specifically, it is known to have a combination pacing, cardioversion, defibrillation and sensing lead implanted into the ventricle, and a large surface area patch electrode affixed to or near the exterior surface of the heart, both of which are connected to a pacemaker and/or a defibrillator. Additional pacing systems may also include a transvenous lead passively implanted into the coronary sinus, in addition to a lead which provides only sensing within the atrium. With this type of system, there may be three or more different pacing, cardioversion, defibrillation or sensor leads extending intravenously into the interior of the heart, in addition to a patch lead and electrode affixed to or near the epicardial surface of the heart, all connected to the pacemaker and/or defibrillator.

During the implantation procedure, the attending physician may implant a combination lead having pacing and sensing electrodes, which also includes a defibrillation electrode mounted proximally of the distal tip, and then test whether the defibrillation electrode can provide sufficient energy to defibrillate the heart. In the event that defibrillation requires too much energy or cannot be accomplished by the combination lead, a second lead may be implanted into the coronary sinus to act as either a cathode or anode for bipolar defibrillation and/or pacing or sensing between the coronary sinus lead and the combination transvenous lead placed in the right ventricle.

The physician may then determine the necessary electrical charge to defibrillate using the bipolar system, and determine whether or not a patch electrode must also be affixed to or near the epicardial surface of the heart or nearby, such as in a subcutaneous or subcostal site. If such a patch electrode is also required, following affixation of the patch electrode, the attending physician may test various bipolar combinations of the three leads for defibrillating the heart, using alternatively the patch electrode, the coronary sinus lead, and/or the electrode on the combination lead as the cathode(s) or anode(s) to determine the lowest threshold for defibrillation. Thus, while it may be necessary to have the patch electrode affixed to or near the exterior surface of the heart (or subcutaneously or subcostally near the heart), preferably if defibrillation can occur by the use of a combination pacing and defibrillation electrode placed in the right ventricle, and a coronary sinus electrode, the necessity for opening the chest cavity and affixing the patch electrode on or near the heart may be avoided.

When utilizing a coronary sinus lead electrode in conjunction with a pacing lead electrode to accomplish pacing, cardioversion or defibrillation, it is important to recognize that preserving the atrial-ventricle synchronization, by proper timing of the respective contractions, is very important to prevent the patient from adverse effects resulting from asynchronous contractions. Thus, in addition to providing the necessary pacing and defibrillation charges, it is extremely beneficial to have a system which can effectively preserve synchronization of the atrial and ventricle contractions by properly sensing the atrial depolarization and properly timing the electrical stimulus to the ventricle.

One method of obtaining the additional sensory information required to provide synchronization has been through the utilization of a separate atrial sensing lead, to provide sensing within the atrial cavity which provides additional information to the pacemaker. The atrial sensing lead may simply be implanted and allowed to freely float within the atrial cavity. Disadvantages of having a third intravenously implanted lead, include the fact that more hardware is implanted, perhaps to the detriment of cardiac function and optimal blood flow, in addition to the potential problems with its placement or implant location.

Accordingly, it would be very beneficial to provide a pacing system and cardioversion or defibrillation system which utilizes an improved coronary sinus lead electrode having the capability of being able to sense atrial electrical activity, thereby assisting the preservation of the atrial/ventricular synchronization while eliminating the need for an additional atrial sensing lead.

SUMMARY OF THE INVENTION

The present invention details a coronary sinus lead, for use in combination with an implanted pulse generator which may be a pacemaker or defibrillator or combination thereof. The coronary sinus lead can deliver an electrical charge to pace, cardiovert or defibrillate the heart. In addition, the coronary sinus lead can sense cardiac activity in the coronary sinus of the heart. The coronary sinus lead may also include sensor electrodes capable of sensing stimuli in the atrial cavity, including atrial electrical activity, fluid flow, and pressure, with the use of one or more atrial sensing electrodes. The coronary sinus lead allows cardioversion and/or defibrillation stimuli to be provided by a large surface area electrode which is passively implanted in the coronary sinus, while also sensing atrial activity, to allow the pulse generator to provide appropriately synchronized atrial-ventricular pacing, cardioversion or defibrillation.

BRIEF DESCRIPTION OF THE DRAWINGS

FIG. 2 depicts an enlarged view of the proximal end of the coronary sinus lead of FIG. 1;

FIG. 3 depicts an enlarged view of the distal end of the coronary sinus lead of FIG. 1;

DETAILED DESCRIPTION OF THE PREFERRED EMBODIMENT

Figure 1:
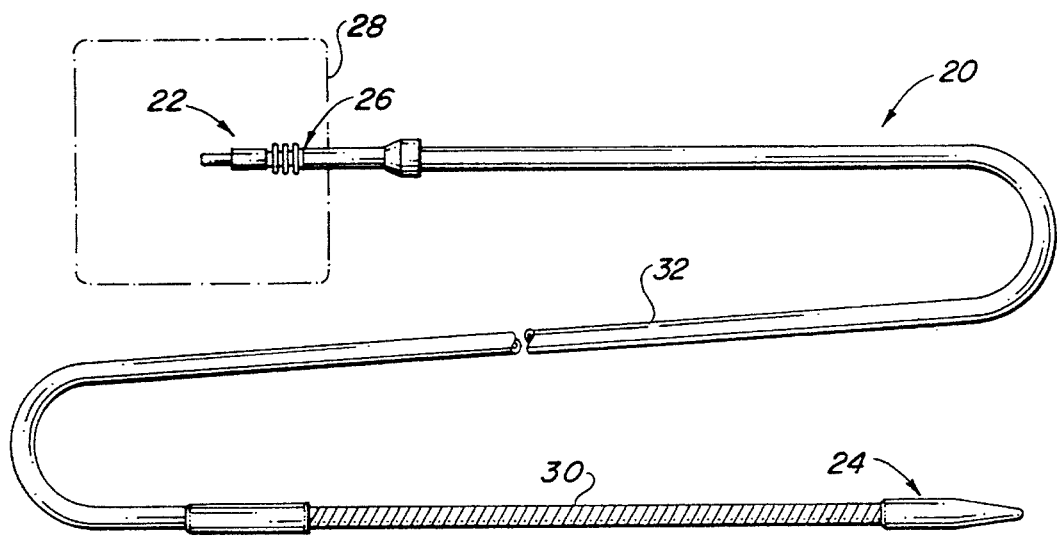
FIG. 1 depicts a coronary sinus lead and pulse generator according to the present invention.

FIG. 1 depicts a coronary sinus lead 20 according to the present invention. The coronary sinus lead 20 includes a proximal end 22 and a distal end 24. At the proximal end 22, a connector assembly 26 accommodates interconnection with an implanted signal processing and pulse generator means, such as a pacemaker 28 and/or defibrillator. At the distal end 24 of the coronary sinus lead 20 is located a coronary sinus defibrillation electrode 30. A lead body 32 interconnects the proximal end 22 and the distal end 24 of the coronary sinus lead 20.

The detailed construction of the proximal end 22 of the sinus lead 20, including the connector assembly 26, is illustrated in the cross-sectional view of FIG. 2. The connector assembly 26 includes a connector pin 34 extending into a connector boot 36. The connector pin 34 is securely interconnected to an electrical conductor 38 as illustrated by laser welds or crimps 40. The connector boot 36 is preferably formed from a biocompatible plastic or elastomeric material such as, for example, silicon, and may include a plurality of sealing rings 44 and a connector grip area 46 extending a short distance from the connector pin 34. The conductor 38 is preferably encased in an insulation material 50. The conductor 38 is preferably a helically wound coil of multifilar conductors which are braided about a silver core (not shown). Preferably, the helically wound coil defines a hollow central portion, extending through the center of the helix, which is in open communication with an axial bore in the connector pin 34, allowing for the insertion of a stylet 48 or guidewire useful for allowing the proper implanting of the coronary sinus lead 20.

FIG. 3 depicts an enlarged cross-sectional view of the distal end 24 of the coronary sinus lead 20. In FIG. 3, the sinus electrode 30 is illustrated as being a coil 74 wrapped about a sleeve 76. Preferably, the coil 74 and sleeve 76 of the sinus electrode 30 are formed from a platinum-iridium material. However, the sleeve 76 may be formed from a flexible insulation material, whereby the coil 74 must be directly coupled to the conductor 38. Preferably, the sleeve 76 is conductive and is electrically connected to the conductor 38 extending into and potentially through the central portion of the sleeve 76. At the distal end 24, a rubber tip 88 is inserted over the end of the conductor 38 and affixed to a connector element 90. The connector element 90 is preferably securely affixed to the coil 74 of the sinus electrode 30, as well as to the sleeve 76. The tip 88 is preferably formed from a silicone rubber material, and tapers to a point 96. At the proximal end of the electrode 30, opposite the tip 88, is a connector element 98 which allows interconnection of the sinus electrode 30 including coil 74, as well as sleeve 76, to the insulation material 50 about the conductor 38. The connector element 98 includes an axial bore through which the conductor 38 passes prior to entering the central portion of the sleeve 76.

Figure 4:
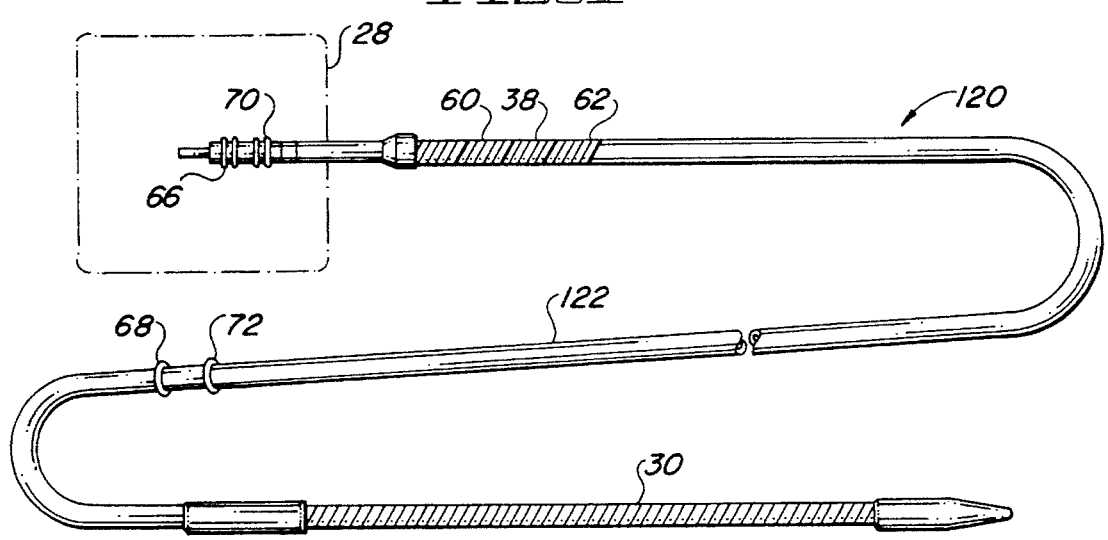
FIG. 4 is an alternative embodiment of a coronary sinus lead including sensor electrodes placed proximally of the distal end of the lead.

In FIG. 4, an alternative design for a coronary sinus lead 120 is depicted. The coronary sinus lead 120 includes a majority of the same elements discussed and numbered above. As in FIG. 1, the conductor 38 interconnects to the sinus electrode 30 near the distal end 24 of the coronary sinus lead 20. In addition, a second or even third conductor 60, 62 may extend the length of the lead body 122 as shown in FIG. 4. Thus, conductor 60 may interconnect a ring connector 66 and a sensing electrode 68, while conductor 62 may interconnect a ring connector 70 and sensing electrode 72. The electrodes 68 and 72 are located distally of the electrode 30, while the ring connectors 66 and 70, respectively are located distally of the connector pin 34 in the connector assembly 22. The ring electrodes 68, 72 are preferably spaced from the sinus electrode 30 a distance of between 1 and 5 centimeters.

Figure 5:
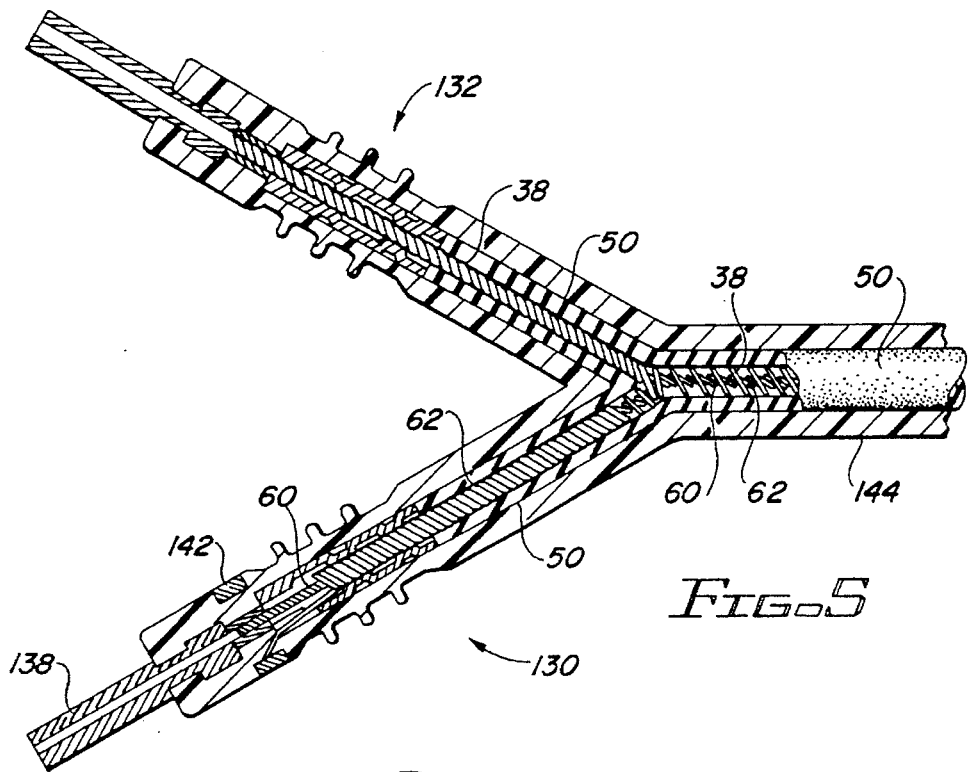
FIG. 5 depicts an alternate configuration for the connector assembly of the sinus lead according to FIG. 4.

For the sinus lead 120 having atrial sensing capability illustrated in FIG. 4, the proximal end of the sinus lead 120 may require a second connector assembly 130 which splits off from a primary connector assembly 132, as illustrated in FIG. 5. In this configuration, the conductors 60, 62 extending to the sensor electrodes 68 and 72 are terminated at a pin connector 138 and ring connector 142, respectively, in a manner which facilitates allowing the two connectors assemblies 130, 132 to plug into a pacemaker and/or a defibrillator having two connector receiving orifices designed to receive a first connector for a coronary sinus lead and a second connector for an atrial sensor lead. As illustrated in FIG. 5 the insulated cables extending from the primary and secondary connectors 132, 130, merge into a single lead body 144, which is essentially identical to the lead body 122 of sinus lead 120 of FIG. 4.

Figure 6:
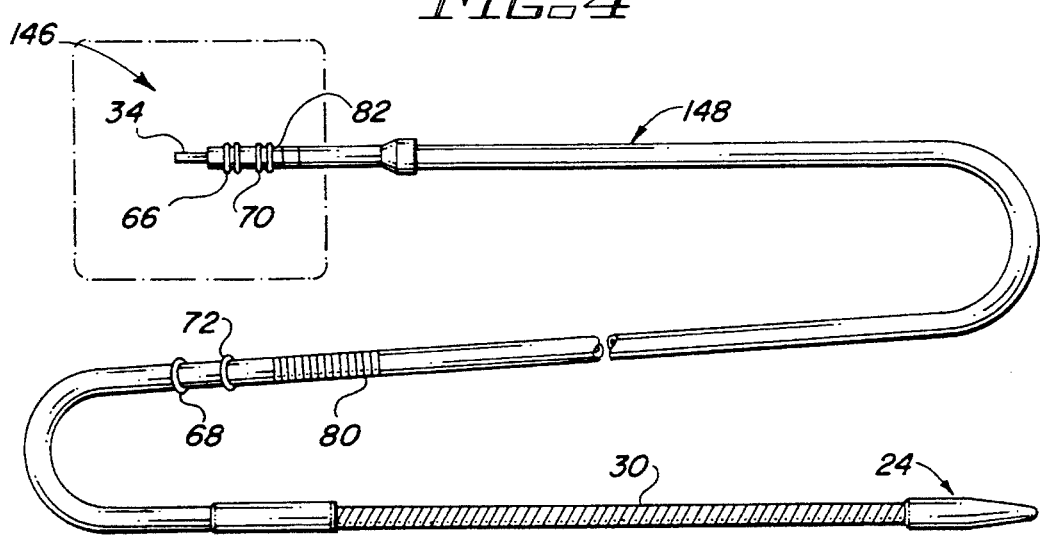
FIG. 6 depicts an alternative design for a coronary sinus lead including a second defibrillation electrode.

FIG. 6 depicts another alternative design for a sinus lead 148. The sinus lead 148 includes the sinus electrode 30 proximally of the distal end 24, as well as the pair of sensor electrodes 68 and 72 located proximally of the proximal end of the sinus electrode 30. In addition, the sinus lead 148 includes a vena cava electrode 80 spaced proximally of the two sensor electrode 68 and 72. The vena cava electrode 80 is preferably designed similar to the design of the sinus electrode 30, with a central core sufficiently large to allow pass through of the conductors which terminate at the ring electrodes and sinus electrode 30. The vena cava electrode 80 is intended to act as an anode in a bipolar defibrillation system using the sinus electrode 30 as the cathode. Furthermore, it may be beneficial to defibrillate using the vena cava electrode 80 as the cathode and the sinus electrode 30 as the anode, or alternatively, utilize a second electrode which may be a patch electrode or an electrode on a pacing lead as the second pole in a bipolar pacing, cardioversion or defibrillation arrangement.

The sinus lead 148 of FIG. 6 includes a connector assembly 146 at its proximal end. The connector assembly 146 includes a pin connector 34, ring connectors 66 and 70 and a ring connector 82. The ring connector 82 is connected via a conductor within and passing through the lead body to the vena cava electrode 80. The remaining electrodes and connectors are essentially interconnected as described above by three separate conductors extending through the lead body. Following implant of the sinus lead 148, the sinus electrode 30 will be positioned within the coronary sinus vein, the sensor electrodes 68 and 72 will preferably be positioned within the atrial cavity, and the vena cava electrode 80 will preferably be positioned close to the atrial wall or even within the vena cava. Via this assembly, a pacing, cardioversion or defibrillation charge applied via the sinus electrode 30 or alternatively via a patch electrode will traverse a substantial portion of the heart before reaching the anode vena cava electrode 80.

For any of the foregoing embodiments, the sinus electrode 30 may include a coating deposited on the coil 74, the material for the coating being platinum black, carbon, titanium, or titanium nitride. The sinus electrode 30 has a total surface area in the range of between about 0.5 and 10 square centimeters, with a preferred size of between 2 and 4 square centimeters. In addition, the vena cava electrode 80 which is positioned in the vena cava, may have a surface area in the range of between about 0.5 and 10 square centimeters, with a preferred size of between 3 and 5 square centimeters.

In addition or in the alternative, the sinus electrode 30 may be coated with a biocompatible, hypo-inflammatory material. Preferred biocompatible, hypo-inflammatory materials which can be used as coatings include soluble starches such as amylodextrin and amylogen, proteins such as collagen, albumin and gelatin. These protein materials may be cross-linked with a crosslinking agent such as 1-ethyl-3-(3-dimethylaminopropyl), carbodiimide, hydrochloride. Additionally, ion exchange materials such as polyethylenimine, poly-sodium styrenesulfonates, and sulfonated polytetrafluoroethylene sold under the tradename NAFION by the DuPont Corporation. These materials are preferred because of the ability of the body to resorb them without adverse effect.

Polymeric systems including polyethylene oxide or glycol, polypropylene oxide or glycol, polypropylene glycol, polysorbates, poly-vinylalcohol, and copolymers of ethylene oxide/propylene oxide can also be used as the coating material, and can deliver therapeutic agents by co-dissolution due to the inherent solubility of these materials.

The coating material is preferably a mixture of one of the above materials blended with an anti-inflammatory agent such as fluoro-trihydroxy-methyl pregna diene/dione or fluoro-methylprednisolone, sodium phosphate, the sodium salt of methoxy-methylnaphthalene-acetic-acid, sodium, or the sodium salt or forms of dexamethasone sodium phosphate of isobutylphyl-propionic acid. The anti-inflammatory agents can constitute between about 1% to 95% by weight of the coating material, preferably however, the anti-inflammatory agents constitute in the range of between 5% and 50% by weight of the coating material.

Figure 7:
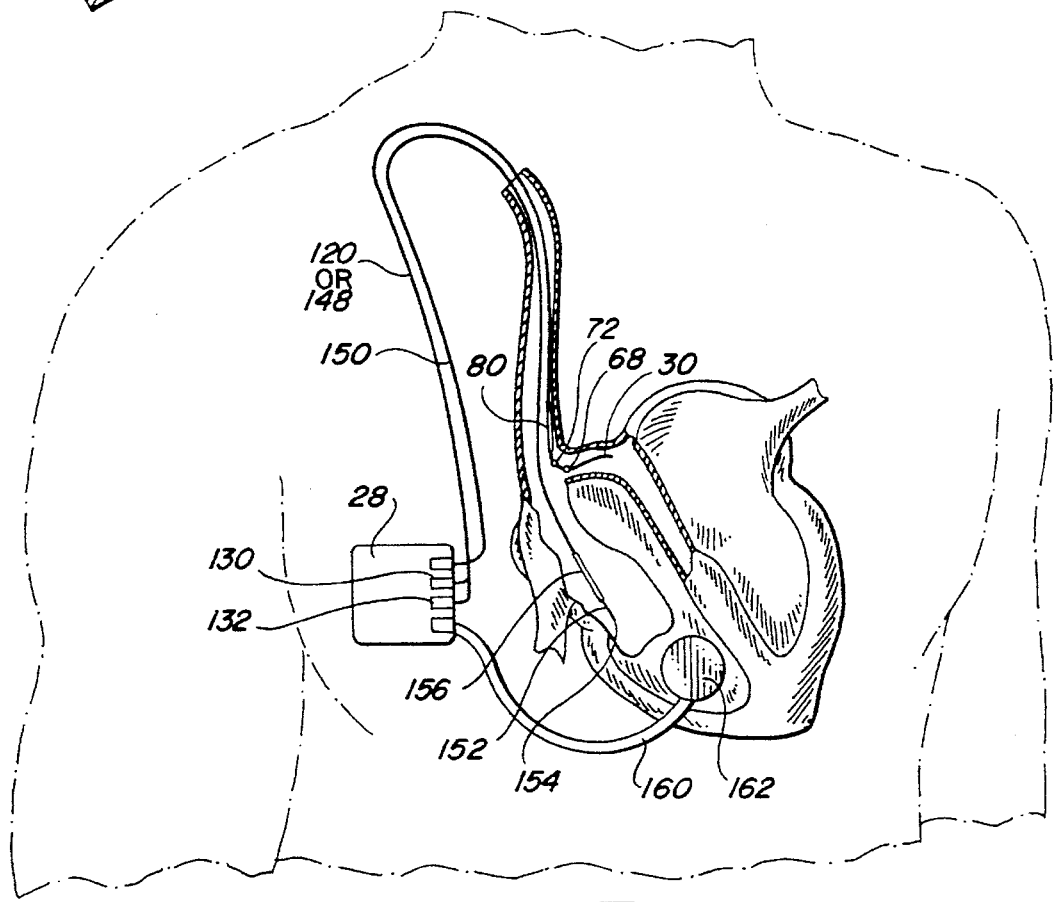
FIG. 7 depicts an implanted pulse generator interconnected via plural leads, including the coronary sinus lead of FIG. 6, to a heart.

FIG. 7 depicts a partially cut-away view of an implanted signal processing and pulse generating means such as a pacemaker 28 interconnected via a pacing lead 150, a coronary sinus lead 20 (or 120 or 148), and a patch electrode lead 160 to a heart. The pacing lead 150 is illustrated as being transvenously inserted and extending to the right ventricle. The pacing lead 150 includes an electrode assembly 152 which may, for example, include a tip electrode 154 in combination with a coil electrode 156. The tip electrode 154 is preferably used with the pacemaker 28 to provide a pacing electrical output to the heart, and also to sense normal pacing electrical activity, in either a unipolar or bipolar arrangement. If a bipolar arrangement is used for pacing, the tip electrode 154 may act as the cathode with the sinus electrode 30 of the sinus lead 20 acting as the anode. For defibrillation, the coil electrode 152 of the pacing lead 150 may act as the cathode with the sinus electrode 30 of the sinus lead 20 acting as the anode. Alternatively, the sinus electrode 30 of the sinus lead 20 could be utilized as the cathode with the coil electrode 156 of pacing lead 150 acting as the anode.

As further illustrated in FIG. 7, the patient may also have the patch electrode lead 160, which terminates at a patch electrode 162 affixed to the epicardial surface of the heart, to provide a large electrode useful for acting as either the anode or cathode in a unipolar or bipolar cardioversion or defibrillation. It may also be placed near the heart in a subcostal or subcutaneous site. The patch electrode lead 162 is also interconnected to the pacemaker 28.

For a patient which is equipped with all three of the leads depicted in FIG. 7, cardioversion or defibrillation can be accomplished by any combination of the primary electrodes, including the coil electrode 156 of pacing lead 150, the sinus electrode 30 or vena cava electrode 80 of sinus lead 20 or patch electrode 162 of patch electrode 160. While given a sufficient charge, any combination of the four foregoing primary electrodes would operate to defibrillate a heart, a key aspect of minimizing the battery drain required for a defibrillation or cardioversion requires that the attending doctor determine which combination of electrodes will result in the lowest current threshold required for defibrillation. Thus, the doctor may sequentially test the defibrillation threshold using each of the major electrodes successively as the cathode and/or anode.

In view of the foregoing detailed description, the present invention contemplates a method of delivering an electrical stimulus to a heart. The method includes implanting a pulse generator, implanting a coronary sinus lead extending through a vein and terminating at a sinus electrode positioned within the coronary sinus vein of the heart, sensing the electrical activity of the heart, and delivering an electrical charge generated by the pulse generator through the coronary sinus lead and the sinus electrode to the heart. The method further contemplates delivering the electrical stimulus so as to maintain ventricular-atrial synchronization. Additionally, the method also contemplates sensing atrial activity utilizing sensor electrodes located on the coronary sinus lead proximally spaced from the sinus electrode.

The method of delivering an electrical stimulus to a heart may further contemplate transvenously implanting a pacing lead extending from the pulse generator through a vein into the ventricle, the pacing lead including an electrode, and operating the electrode of the pacing lead and the sinus electrode in combination with the pulse generator to define a bipolar electrical charge delivery system capable of pacing, cardioverting and defibrillating. The bipolar pacing system is preferably controlled in a manner to maintain ventricular-atrial synchronization. The foregoing methods may also require affixing a patch electrode to the epicardial surface of the heart or placing it subcostally or subcutaneously, interconnecting the patch electrode to the pulse generator, and operating the sinus electrode and the patch electrode in cooperation with the pulse generator as a bipolar charge delivery system to pace, defibrillate or cardiovert the heart.

It should be evident from the foregoing description that the present invention provides many advantages over coronary leads and pacing or defibrillating systems of the prior art. Although preferred embodiments are specifically illustrated and described herein, it will be appreciated that many modifications and variations of the present invention are possible in light of the above teaching to those skilled in the art. It is preferred, therefore, that the present invention be limited not by the specific disclosure herein, but only by the

What is claimed is:

1. An apparatus for pacing, cardioverting or defibrillating a heart comprising:

an implantable pulse generator;

a coronary sinus lead connected at a proximal end to said pulse generator comprising a lead body including at least two conductors encased within an insulation material, said coronary sinus lead having a coronary sinus defibrillating electrode at its distal end, the coronary sinus defibrillating electrode including an electrically conductive coil wrapped about an electrically conductive sleeve, at least one of said conductors of said lead body extending into said electrically conductive sleeve and electrically connected thereto; and sensor means for sensing physical or electrical parameters in the atrial cavity, said sensor means attached to said coronary sinus lead.

2. The apparatus of claim 1, wherein said coil of said coronary sinus defibrillating electrode is formed from a platinum-iridium wire.

3. The apparatus of claim 2, wherein said coil of said sinus electrode coil includes a coating deposited on the electrode coil, the material for said coating being selected from the group consisting of platinum black, carbon, titanium and titanium nitride.

4. The apparatus of claim 1, wherein said atrial sensor means comprises at least one ring electrode spaced proximally from the proximal end of said coronary sinus defibrillating electrode, and said lead body includes at least one conductor interconnected to said coronary sinus defibrillating electrode, and at least one conductor interconnected to each of said at least one ring electrode, each of said conductors extending the length of said lead body and terminating at a respective electrical connector located at the proximal end of said coronary sinus lead.

5. The apparatus of claim 4, wherein said at least one ring electrode is spaced from the coronary sinus defibrillating electrode a distance of between 1 and 5 centimeters.

6. The apparatus of claim 4, wherein the proximal end of said coronary sinus lead terminates at a connector assembly, said connector assembly including:

an electrical connector electrically attached to the end of said conductor extending to said coronary sinus defibrillating electrode; and at least one ring connector spaced distally of said electrical connector, said at least one ring connector being electrically connected to said at least one conductor extending to said at least one ring electrode.

7. The apparatus according to claim 4, wherein said coronary sinus lead further comprises:

a first connector assembly including an electrical connector attached to said conductor which extends to said coronary sinus defibrillating electrode, said electrical connector adapted for insertion into said pulse generator; and a second connector assembly including at least one electrical connector, said second connector having said electrical connector interconnected to said at least one conductor extending to said at least one ring electrode, said lead body forming a "Y" near its proximal end so as to terminate in said first and second connector assemblies.

8. The apparatus of claim above 1, wherein said coronary sinus defibrillating electrode is coated with a biocompatible, hypo-inflammatory material.

9. The apparatus of claim 8, wherein said coating material on said coronary sinus defibrillating electrode is a material selected from the group consisting of hydrogels, polymeric systems, soluble starches, proteins and ion exchange materials.

10. The apparatus of claim 1, wherein said coronary sinus defibrillating electrode has a total surface area in the range of between about 0.5 and 10 square centimeters.

11. The apparatus of claim 1, wherein said coronary sinus defibrillating electrode includes a sensing electrode for sensing an electrical signal indicative of electrical activity in the coronary sinus.

12. The apparatus of claim 1, wherein said coronary sinus lead has a soft flexible nonconductive tip affixed to the distal end of said coronary sinus lead.

13. The apparatus of claim 12, wherein said soft flexible nonconductive tip tapers to a blunt end at the distal tip of said coronary sinus lead.

14. The apparatus of claim 1, wherein said coronary sinus lead comprises a multifilar coil comprising a plurality of wires formed of a noncorroding conductive alloy with a silver core.

15. A coronary sinus lead adapted for connection to an implantable pulse generator, said coronary sinus lead comprising;

a lead body;

a connector located at a proximal end of said lead body, said connector adapted to interconnect to said pulse generator; and a coronary sinus defibrillating electrode positioned near the distal end of said lead body, said coronary sinus defibrillating electrode configured to be passively implanted in the coronary sinus vein of a heart, wherein said coronary sinus defibrillating electrode includes an electrically conductive coil wrapped about an electrically conductive sleeve, said conductor of said lead body extending into said sleeve and electrically connected thereto.

16. The coronary sinus lead of claim 15, further comprising at least one ring electrode spaced proximally of a proximal end of said coronary sinus defibrillating electrode, said at least one ring electrode operative to sense physical or electrical parameters and the atrium of the heart and to produce an output signal.

17. The coronary sinus lead of claim 16, further comprising a vena cava defibrillating electrode spaced proximally of said at least one atrial sensing ring electrode.

18. The coronary sinus lead of claim 15, further comprising a vena cava defibrillating electrode spaced proximally of a proximal end of said coronary sinus defibrillating electrode.

19. The coronary sinus lead of claim 15, wherein said coronary sinus lead further comprises a lead body including at least one conductor encased within an insulation material.

20. The coronary sinus lead of claim 15, wherein said coil of said sinus electrode is formed from a platinum-iridium wire.

21. The coronary sinus lead of claim 15, wherein said coil of said sinus electrode coil includes a coating deposited on the electrode coil, the material for said coating being selected from the group consisting of platinum black, carbon, titanium and titanium nitride.

22. The coronary sinus lead of claim 15, wherein said sinus electrode is coated with a biocompatible, hypo-inflammatory material.

* * * * *